United States Patent [19]

Kotera et al.

[11] Patent Number: 4,612,394
[45] Date of Patent: Sep. 16, 1986

[54] PROCESS FOR PRODUCING AMINOPHENYL-β-HYDROXYETHYLSULFONE

[75] Inventors: Norio Kotera, Amagasaki; Kazuhiro Tada, Kyoto; Shinzaburo Masaki, Ashiya; Kunihisa Goto, Kurashiki; Tatsuo Kaneoya, Toyonaka, all of Japan

[73] Assignee: Sumitomo Chemical Company, Limited, Osaka, Japan

[21] Appl. No.: 477,443

[22] Filed: Mar. 21, 1983

[30] Foreign Application Priority Data

| Apr. 6, 1982 [JP] | Japan | 57-57483 |
| Apr. 6, 1982 [JP] | Japan | 57-57484 |
| Apr. 6, 1982 [JP] | Japan | 57-57485 |
| Apr. 6, 1982 [JP] | Japan | 57-57486 |

[51] Int. Cl.⁴ .............................................. C07C 85/11
[52] U.S. Cl. ................................... 564/420; 564/418; 564/421; 564/422; 564/423; 564/440; 564/443; 568/30; 568/31; 568/44; 423/584
[58] Field of Search ............... 564/420, 421, 422, 423, 564/418, 443, 440; 568/30, 31, 44; 423/584

[56] References Cited

U.S. PATENT DOCUMENTS

| 3,005,852 | 10/1961 | Freyermuth et al. | 568/30 |
| 3,019,266 | 1/1962 | Buc et al. | 568/30 |
| 3,019,268 | 1/1962 | Buc et al. | 568/30 |
| 4,133,869 | 1/1979 | Kim | 423/584 |

FOREIGN PATENT DOCUMENTS

| 57-48962 | 3/1982 | Japan |  |
| 57-58662 | 4/1982 | Japan | 568/44 |

*Primary Examiner*—Charles F. Warren
*Attorney, Agent, or Firm*—Stevens, Davis, Miller & Mosher

[57] ABSTRACT

A process for producing aminophenyl-β-hydroxyethylsulfone of the formula (I),

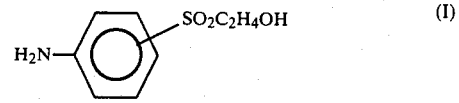

which comprises the following steps:

(1) condensing nitrohalobenzene with mercaptoethanol in the presence of an alkali hydroxide and at least one reaction medium selected from N-alkyl-substituted amides and sulfoxides to produce mononitrophenyl-β-hydroxyethylsulfide of the formula (II):

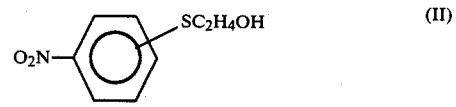

(2) oxidizing the mononitrophenyl-β-hydroxyethylsulfide (II) to produce mononitrophenyl-β-hydroxyethylsulfone of the formula (III):

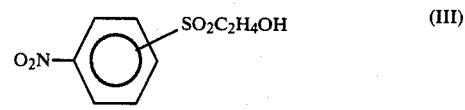

and (3) reducing the mononitrophenyl-β-hydroxyethylsulfone to produce the aminophenyl-β-hydroxyethylsulfone of the formula (I). This compound is useful as an intermediate for aminophenyl-β-sulfatoethylsulfone represented by the following formula:

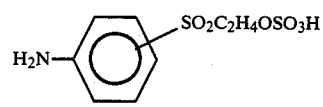

which is an important intermediate for vinyl sulfone type reactive dyes largely used for dyeing cellulose fiber materials.

11 Claims, No Drawings

PROCESS FOR PRODUCING AMINOPHENYL-β-HYDROXYETHYLSULFONE

The present invention relates to a process for producing aminophenyl-β-hydroxyethylsulfone.

More particularly, the invention relates to a process for producing aminophenyl-β- hydroxyethylsulfone useful as an intermediate for aminophenyl-β-sulfatoethylsulfone represented by the following formula,

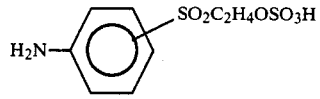

which is an important intermediate for vinylsulfone type reactive dyes largely used for dyeing cellulose fiber materials.

The aminophenyl-β-sulfatoethylsulfone has been produced by reacting aniline with acetic anhydride to produce acetoanilide, followed by chlorosulfonating the latter with a largely excessive quantity of chlorosulfonic acid to produce acetylaminobenzenesulfonyl chloride, reducing the latter with sodium sulfite to produce the corresponding sulfinic acid, reacting the latter with ethylene oxide or ethylene chlorohydrin to produce acetylaminophenyl-β-hydroxyethylsulfone, and then subjecting the latter to hydrolysis and esterification in sulfuric acid to obtain the desired sulfuric ester.

However, the above-mentioned prior process is not always industrially advantageous industrially, because its industrial practice is accompanied with the following problems:

(1) The chlorosulfonation reaction in chlorosulfonic acid is essentially an equilibrium reaction, so that a largely excessive amount of chlorosulfonic acid is necessary for suppressing the formation of acetylaminobenzenesulfonic acid as a by-product.

(2) The excessive chlorosulfonic acid is difficult to recover, so that it must be disposed as an acidic wastewater ultimately at a huge cost.

(3) The acetylaminobenzenesulfonyl chloride which is unstable causes lowering of the product yield.

(4) The reduction into sulfinic acid using sodium sulfite gives only a low yield, because of instability of the sulfinic acid.

(5) In the final step, free acetic acid formed upon hydrolysis of the acetyl group reacts with the hydroxyl group of the hydrolyzate to yield an acetic ester compound as a by-product which lowers the purity of the product. Further, the free acetic acid existing in the system causes problems, such as corrosion of reactor, problem of wastewater disposal, and so on.

With the aim of discovering an industrially advantageous process for producing aminophenyl-β-hydroxyethylsulfone which is an intermediate for the aminophenyl-β-sulfatoethylsulfone, the present inventors studied a process for producing aminophenyl-β-hydroxyethylsulfone represented by the following formula (I),

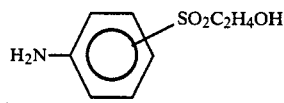

which comprises a step for reacting a nitrohalobenzene with mercaptoethanol in the presence of an alkali to produce mononitrophenyl-β-hydroxyethylsulfide represented by the following formula (II),

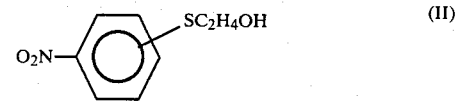

a step for oxidizing the sulfide (II) to produce a sulfone compound represented by the following formula (III),

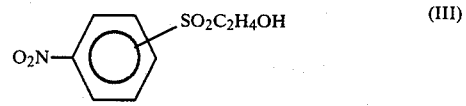

and a step for reducing said sulfone compound (III).

The reaction between a nitrohalobenzene and mercaptoethanol is referred to in a few papers, including J. Amer. Chem. Soc. Vol. 55, Page 4956 (1933); J. Chem. Soc. (1927) Pages 1666–1676; and Kogyo Kagaku Zasshi, Vol. 62, Pages 825–828. However, the cases found in these papers are limited to reaction between o-nitrochlorobenzene and mercaptoethanol in an alcoholic solvent in the presence of potassium hydroxide. Moreover, an experiment in accordance with the description of these papers revealed that the intended sulfide derivative could be obtained only in a low yield due to the formation of a large amount of azoxy type by-product probably attributable to reaction of nitro group.

Regarding nitrohalobenzenes other than o-nitrochlorobenzene, another synthetic process, i.e. reaction between nitrothiophenol and ethylene chlorohydrin, is recommended because it gives a better yield. However, synthesis of the starting nitrothiophenol requires a strict control of reaction conditions. In addition, the resulting nitrothiophenol is quite unstable and very susceptible to oxidation reaction yielding a disulfide. Thus, the yield of nitrothiophenol is very low, and the process cannot be advantageous as an industrial production process.

In such circumstances, the inventors determined that the key for accomplishing an industrially advantageous production process of the compound of formula (I) consists in finding out the possibility of conducting the condensation step, i.e. the reaction between nitrohalobenzene and mercaptoethanol, so as to result in a product of high purity and high yield. As the result of elaborated studies, the inventors found that the object can be achieved by effecting the condensation reaction in a specified reaction medium in the presence of a specified alkali.

Further, it was unexpectedly found that the water content in the reaction medium is a very important factor for practicing the condensation reaction smoothly and for giving a high yield.

Thus, the present invention provides a process for producing aminophenyl-β-hydroxyethylsulfone of the formula (I), which comprises the following steps:

(1) condensing a nitrohalobenzene with mercaptoethanol in the presence of an alkali hydroxide and at least one reaction medium selected from N-alkyl-substituted amides and sulfoxides to produce mononitrophenyl-β-hydroxyethylsulfide of the formula (II), (2) oxidizing the mononitrophenyl-β-hydroxyethylsulfide (II) to produce mononitrophenyl-β-hydroxyethylsulfone of the formula (III), and (3) reducing the mononitrophenyl-β-hydroxyethylsulfone (III) to produce the aminophenyl-β-hydroxyethylsulfone of the formula (I).

The process of the present invention is illustrated below concretely.

The nitrohalobenzene usable in the condensation step of the process of the invention includes, for example, p-nitrochlorobenzene, o-nitrochlorobenzene, p-nitrobromobenzene and o-nitrobromobenzene.

Said nitrohalobenzenes may be used alone or in a mixture of two or more.

Among these nitrohalobenzenes, nitrochloro-benzenes are preferable.

The alkali hydroxide usable in the condensation step includes, f.or example, alkali metal hydroxides such as sodium hydroxide and potassium hydroxide.

These alkali metal hydroxides are used in an amount ranging from 1.0 through 1.2 moles, preferably from 1.0 through 1.1 moles, per mole of the nitrohalobenzene.

If the amount of alkali hydroxide is larger than 1.2 moles per mole of the nitrohalobenzene, the yield and purity of the intended product drop due to the formation of many by-products such as azoxy compounds attributable to the reaction of nitro group.

Mercaptoethanol is used in an amount ranging from 1.0 through 3 moles, preferably from 1.05 through 2.0 moles, per mole of the nitrohalobenzene.

The reaction medium used in the condensation step is at least one member selected from N-alkyl-substituted amides such as dimethylformamide, N-methyl-2-pyrrolidone, dimethylacetamide and the like, sulfoxides such as sulfolane, dimethyl sulfoxide and the like. These solvents may be used each alone or in a mixture of two or more members. Preferable organic solvents are dimethyl sulfoxide and N-alkyl-substituted amides. Of these, dimethylformamide is particularly preferable.

Amounts of the organic solvent used somewhat vary depending upon the kind of solvent, the solubility of starting nitrohalobenzene in the solvent and so on. Usually, the amount ranges from 0.2 part by weight through 15 parts by weight per part by weight of the starting nitrohalobenzene. A preferable amount is from 0.5 through 10 parts by weight, more preferably from 0.5 through 5 parts by weight per part by weight of the starting nitrohalo-benzene. 10 In practicing the reaction by using this reaction medium, the reaction proceeds quite smoothly to give the desired product in a high yield if the reaction medium contains water in an amount ranging from 2 through 30% by weight. If the water content exceeds 30%, the solubility of the starting nitrohalobenzene is decreased so that the reaction is retarded and, moreover, undesirable side reactions are promoted. If the water content is less than 2%, the alkali hydroxide initially added remains undissolved in the reaction medium, so that the reaction in the early stage is greatly retarded and the alkali hydroxide successively added is increasingly accumulated in the reaction system. Therefore, when the reaction proceeds to some extent, water is produced as a by-product and the alkali hydroxide existing in the system dissolves in the water. Then, the reaction proceeds too rapidly and becomes difficult to control. As the result, the reaction temperature exceeds a preferable range, which not only lowers product yield but also can incur a dangerous state of affairs in industrial practice.

In the present invention, a predetermined amount of water may be added beforehand to the organic solvent.

Alternatively, the water may be introduced into the reaction system together with the alkali hydroxide.

The reaction temperature varies within a range from about 30° to 55° C., preferably 35° to 50° C., depending upon the kinds of nitrohalobenzene and alkali hydroxide.

Although the reaction time varies depending upon reaction temperature and kind of starting materials, it is usually in a range from about 1 to 15 hours, preferably from 2 to 8 hours. An unnecessarily prolonged reaction time is undesirable, because it promotes side reactions and lowers yield and purity of the product.

As one embodiment for performing the condensation reaction, the process may be carried out by adding predetermined quantities of starting nitrohalobenzene and mercaptoethanol into the organic solvent optionally containing water, heating the system to the intended temperature and thereafter adding a predetermined quantity of alkali hydroxide to reaction system with the advance of the reaction. The alkali hydroxide may be added in the form of its aqueous solution.

As another embodiment, it is also possible to practice the reaction by forming an alkali salt of mercaptoethanol from mercaptoethanol and alkali hydroxide and thereafter adding said alkali salt of mercaptoethanol to the reaction system comprising the nitrohalobenzene and organic solvent.

Further, semi-batch type and continuous type of modes of practice can also be employed as embodiments of the invention.

As the atmosphere of the reaction, air can be used. Aside from it, atmosphere or a stream of inert gas such as nitrogen can also be employed.

The liquid reaction mixture formed by the condensation reaction containing mononitrophenyl-β-hydroxyethylsulfide, may be once subjected to filtration in order to remove the by-product inorganic salt, followed by distillation or the like to recover the organic solvent. Thus, the intended mononitrophenyl-β-hydroxyethylsulfide having a high purity can be obtained in a high yield.

Alternatively, the intended mononitrophenyl-β-hydroxyethylsulfide can be obtained by recovering the organic solvent from the reaction mixture by distillation or some other procedures, pouring the residue into a large quantity of water and separating the intended product by filtration or decantation.

In the next step, this sulfide compound (II) is oxidized to produce the sulfone compound (III).

This method for oxidation includes, for example, those using permanganate, chromic acid, ruthenium tetraoxide, a combination of halogen, hypohalogenous acid and its salt, oxygen, hydrogen peroxide, organic peracid, or the like.

Of these methods, the method using hydrogen peroxide is advantageous from a industrial point of view.

According to this method, the sulfide compound (II) obtained in the preceding condensation step is allowed to react with hydrogen peroxide in the presence of a basic compound or a metallic catalyst in a water medium or an aqueous medium containing at least one nitrile compound, whereby the sulfone compound (III) can be obtained.

When carried out in a water medium, the oxidation is carried out by using a basic compound or a metallic catalyst by adjusting pH value of the initial stage to 3 to 8.

When carried out in an aqueous medium containing at least one nitrile compound, the oxidation is carried out either in the presence of a basic compound while adjusting pH value of the reaction system to 7.5 to 10.5, or in the presence of a metallic catalyst.

From the viewpoint of reaction velocity and yield, the oxidation in an aqueous medium containing a nitrile compound is more preferable.

Examples of the nitrile compound usable in the process of the invention include acetonitrile, propionitrile, butyronitrile and the like. Of course, mixtures of two or more nitrile compounds can also be used. Among these nitrile compounds, acetonitrile is preferably used.

These nitrile compounds can be used in an amount ranging from 0.5 through 10 parts by weight per part by weight of the starting sulfide (II). Although the nitrile compound may be used in an amount exceeding 10 parts by weight, the use of such large amounts of nitrile compound lowers efficiency of industrial scale production and lowers the time-space efficiency. Thus, a preferable amount of nitrile compound ranges from 0.5 through 6 parts by weight, more preferably from 1 through 4 parts by weight, per part by weight of the sulfide compound (II).

The basic compound usable includes alkali metal hydroxides such as sodium hydroxide; alkali metal carbonates such as sodium carbonate; alkali metal hydrogen carbonates such as sodium hydrogen carbonate; and the like. These basic compounds may be used each alone or in a mixture of two or more.

The metallic catalyst effectively usable includes tungsten, molybdenum, vanadium, titanium and chromium catalysts. Of these, the preferred are tungsten, molybdenum and vanadium catalysts.

The tungsten catalyst includes tungstic acid, as well as its alkali metal salts, alkaline earth metal salts and ammonium salt.

The molybdenum catalyst includes molybdic acid, as well as its alkali metal salts, alkaline earth metal salts and ammonium salt.

The vanadium catalyst includes vanadic acid, as well as its alkali metal salts, alkaline earth metal salts and ammonium salt.

The amount of the catalyst used can be varied in a wide range from 0.001% by weight through 10% by weight based on the weight of the starting sulfide (II). In general, however, an amount of 0.1 through 2% by weight is enough for the purpose.

In the process of the invention, the nitrile compound-containing aqueous medium is prepared from the above-mentioned nitrile compound, basic compound or metallic catalyst and water.

The amount of water medium or nitrile compound-containing aqueous medium ranges from 2 through 10 parts by weight, preferably from 3 through 8 parts by weight, per part by weight of the starting sulfide (II). An amount larger than 10 parts by weight is not preferred, because it lowers productivity.

The hydrogen peroxide is used in an amount ranging from 2.1 through 3.5 moles, preferably from 2.1 through 3.0 moles, per mole of the starting sulfide (II).

When the oxidation reaction is carried out in a water medium, the initial pH value is adjusted to 3 to 8, preferably 5 to 6.

When the oxidation reaction is carried out in the presence of a basic compound in the nitrile compound-containing aqueous medium, the pH of the aqueous medium is adjusted to 7.5 to 10.5 throughout the reaction. If the pH value is higher than 10.5, hydrolysis of the starting sulfide is accelerated, and nitrophenol and some other compounds are formed as by-products. Further, self-decomposition of hydrogen peroxide takes place in preference to the oxidation reaction at such higher pH value, which is undesirable from the viewpoint of utilization efficiency of hydrogen peroxide. If pH value is lower than 7.5, the oxidation reaction proceeds too slowly, and particularly, the reaction from the intermediate sulfoxide to the desired sulfone compound (III), is quite slow.

Particularly, a pH value of 7.5 to 8.5 is preferable when the starting sulfide is 2-nitrophenyl-$\beta$-hydroxyethylsulfide, and a pH value of 8.5 to 10 is preferable when the starting sulfide is 4-nitrophenyl-$\beta$-hydroxyethylsulfide.

The aqueous medium may be contaminated by the organic solvent which has been used in the step of producing the starting sulfide(II).

When the oxidation reaction is carried out in water medium, reaction temperature is 30° to 100° C. and preferably 70° to 100° C. When the oxidation is carried out in the nitrile compound-containing aqueous medium, reaction temperature is 30° to 65° C., preferably 35° to 55° C. Reaction temperatures higher than those defined above are not always advantageous, because it induces self-decomposition of hydrogen peroxide. In said preferable range of reaction temperature, the period of time necessary for feeding aqueous hydrogen peroxide is from about 0.5 through 3 hours, and the reaction can be completed by keeping the reaction mixture at that temperature for 0.5 to 6 hours after completion of feeding hydrogen peroxide.

According to one embodiment for performing the oxidation, for example, a basic compound or a metallic catalyst is added to water and thoroughly stirred to give a uniform solution. After adjusting pH value of the solution to a predetermined value, the starting sulfide (II) is added, and a predetermined quantity of hydrogen peroxide is fed at desired temperature, and then the resulting mixture is kept at said temperature to complete the oxidation.

Alternatively, after adding the starting sulfide (II) to an aqueous solution of nitrile, a predetermined quantity of hydrogen peroxide solution is fed at a desired temperature, while a basic compound being added so as to keep pH value of the system at predetermined value. After feeding the hydrogen peroxide solution, the resulting mixture is kept at said temperature to complete the reaction, while keeping pH value at a predetermined value. In this case, said basic compound may also be added in the form of aqueous solution.

Alternatively, after mixing a metallic catalyst with the aqueous nitrile solution under stirring to give a uniform mixture, the starting sulfide (II) is added. Subsequently, a predetermined quantity of hydrogen peroxide solution is fed at desired temperature, and then the resulting mixture is kept at said temperature.

After producing the sulfone compound (III) from the sulfide compound (II) in the above-mentioned manner, the sulfone compound is reduced to produce aminophenyl-$\beta$-hydroxyethylsulfone (I).

This reduction may be carried out by conventional reduction methods, such as iron powder reduction method, alkali sulfide reduction method, catalytic reduction method and the like. Of these methods the method of catalytic reduction with hydrogen using an activated metal catalyst is preferable in view of yield and purity of the product and producibility.

The catalyst usable in said catalytic reduction includes:

(A) Raney type metal catalysts such as Raney's nickel, Raney's copper, Raney's iron and the like;

(B) noble metal catalyst supported on appropriate carrier, such as palladium, rhodium, rubidium, platinum and the like supported on carbon, alumina, silica, precipitated barium sulfate and the like; and (C) other metal catalysts such as stabilized Raney's nickel, oxidized mixture of copper and chromium and the like.

The reduction may be carried out in a reaction medium such as water, methanol, ethanol, n- or isopropanol, dioxane, dipropyl ether, dimethylformamide and the like or a mixture thereof. The reaction medium is used in an amount of 0.5 to 10 parts by weight, preferably 1 to 5 parts by weight, per part by weight of the sulfone compound (III). Although the reaction pressure, i.e. hydrogen pressure is not particularly limited, a pressure of 5 to 60 kg/cm$^2$ is preferable from the viewpoint of reaction velocity. Under this hydrogen pressure, the reduction is carried out at a temperature of 30° to 150° C., preferably 40° to 100° C., for 3 to 12 hours. Thus, the sulfone compound (III) may be nearly quantitatively reduced to give aminophenyl-$\beta$-hydroxyethylsulfone (I) without forming by-product at all.

After completion of the reaction, the catalyst is recovered by filtration, and the catalyst recovered may be reused. By removing the solvent from the reaction mixture by distillation or the like, the intended product is obtained as a free amine.

The above-mentioned process of the present invention for producing aminophenyl-$\beta$-hydroxyethylsulfone (I) is characterized in that individual steps from the starting compound to the final product all give high product yields and therefore the over-all yield is high, the product obtained has a high purity, the intermediates formed in individual steps are stable and easy to handle and the procedure in each step is very easy.

The aminophenyl-$\beta$-hydroxyethylsulfone (I) obtained by the process of the present invention can easily be esterified with sulfuric acid to yield aminophenyl-$\beta$-sulfatoethylsulfone by a conventional process. The resulting aminophenyl-$\beta$-sulfatoethylsulfone has a high purity, so that the dye-forming reaction can be practised quite stably, and the color shade of the dye produced therefrom is stable in every lot.

The invention will be illustrated in more detail with reference to the following examples in no limiting way. In the examples, parts and % mean parts by weight and % by weight, respectively.

EXAMPLE 1

To a mixture consisting of 300 parts of dimethylformamide and 15 parts of water, 300 parts of p-nitrochlorobenzene was added and then 171 parts of mercaptoethanol was added. Temperature of the mixture was elevated to 40° C. in an atmosphere of nitrogen.

Then, 77 parts of powdery sodium hydroxide was added over a period of 4 hours, after which the resulting mixture was kept at that temperature for an additional 2 hours. After completion of the reaction, the reaction mixture was neutralized, water was distilled off at 70° C. under a reduced pressure of 60 mm Hg, and then the dimethylformamide was distilled off while additionally decreasing the pressure. Finally, the residue was kept at 140° C. for 1 hour at a pressure of 10 mm Hg. After returning the system to ordinary pressure, it was cooled to 80° C., 600 parts of water was added, the mixture was stirred at 70° C. for 30 minutes, and then the oily layer (410 parts) was separated. It contained 89% of 4-nitrophenyl-$\beta$-hydroxyethylsulfide. Its yield was 96%.

The oily layer was added to a solution prepared by adding 1 part of sodium tungstate into 370 parts of water and adjusting pH to 5.5, into which was then added dropwise 400 parts of 35% hydrogen peroxide solution at 95° C. over a period of 5 hours. Thereafter, the mixture was kept at that temperature for an additional 2 hours. Subsequently, it was neutralized with 20% aqueous solution of sodium carbonate at a temperature of 85° C., cooled to room temperature, and filtered to obtain 550 parts of wet cake. It contained 74% of 4-nitrophenyl-$\beta$-hydroxyethylsulfone. Its yield was 92% based on p-nitrochlorobenzene.

Then, the wet cake was placed in a stainless autoclave together with 400 parts of methanol and 4 parts of 2% palladium-carbon catalyst (50% wet product) and subjected to reductive hydrogenation reaction at 60° C. for 5 hours at a pressure of 20 kg/cm$^2$. After filtering off solid matters such as catalyst from the reaction mixture, methanol and water were distilled off. Thus, 350 parts of 4-aminophenyl-$\beta$-hydroxyethylsulfone was obtained.

Its yield was 91% based on p-nitrochlorobenzene.

EXAMPLE 2

To 300 parts of dimethylformamide, 300 parts of p-nitrochlorobenzene was added and then 171 parts of mercaptoethanol was added in an atmosphere of nitrogen. The mixture was heated to 35° C.

Then, 160 parts of 48% aqueous solution of sodium hydroxide was added dropwise over a period of 4 hours, after which the mixture was kept at that temperature for an additional 2 hours. After completion of the reaction, the reaction mixture was neutralized with 36% hydrochloric acid, water was distilled off at 70° C. under a reduced pressure of 60 mm Hg, and then dimethylformamide was distilled off while additionally decreasing the pressure. Finally, the residue was kept at 140° C. for 1 hour at a pressure of 10 mm Hg. After returning the system to ordinary pressure, 800 parts of water was added, and the mixture was cooled to room temperature. Filtration gave 450 parts of wet cake. It contained 80% of 4-nitrophenyl-$\beta$-hydroxyethylsulfide. Its yield was 95%.

The wet cake was added to a solution previously prepared by adding 1 part of sodium tungstate to 350 parts of water and adjusting pH to 5.8, into which was then added dropwise 396 parts of 35% hydrogen peroxide solution over a period of 4 hours. Thereafter, the mixture was kept at that temperature for an additional 2 hours. Subsequently, it was cooled, neutralized and filtered to obtain 530 parts of wet cake. It contained 75% of 4-nitrophenyl-$\beta$-hydroxyethylsulfone. Its yield was 90% based on p-nitrochlorobenzene.

Then, the wet cake was placed in a stainless autoclave together with 400 parts of water and 4 parts of 2% palladium-carbon catalyst (50% wet product) and subjected to reductive hydrogenation reaction at 60° C. for 8 hours under a pressure of 20 kg/cm$^2$.

By filtering off solid matters such as catalyst from the reaction mixture and then distilling off the water, 339 parts of 4-aminophenyl-$\beta$-hydroxyethylsulfone was obtained.

Its yield was 88% based on p-nitrochlorobenzene.

EXAMPLE 3

To 80 parts of dimethylformamide having a water content of 5%, 79 parts of o-nitrochlorobenzene was added and then 47 parts of mercaptoethanol was added. Temperature of the mixture was elevated to 50° C. Then, 21 parts of powdery sodium hydroxide was added over a period of 5 hours. After adding it, the resulting mixture was kept at that temperature for an additional 1 hour. After completion of the reaction, the reaction mixture was neutralized, the deposited sodium chloride was filtered off, and the filtrate was distilled to distil off the dimethylformamide. Thus, 96 parts of 2-nitrophenyl-β-hydroxyethylsulfide (III-1) was obtained. Its yield was 96%. Then, (III-1) was added to a mixture of 200 parts of acetonitrile and 100 parts of water, into which was added dropwise 137 parts of 30% hydrogen peroxide solution at 40° C. over a period of 1 hour. During this period, 10% aqueous solution of sodium carbonate was added in order to maintain pH of the system at 8.0. After adding dropwise the hydrogen peroxide solution, the resulting mixture was kept at that temperature for an additional 2 hours, while keeping pH of the system at 8.0.

After completion of the reaction, acetonitrile was distilled off, and the resulting 2-nitrophenyl-β-hydroxyethylsulfone (III-2) was taken out from the system by filtration. Its yield was 103 parts.

Then, (III-2) was subjected to iron powder reduction. Thus, first of all, 5 parts of 98% sulfuric acid was added to a mixture of 300 parts of water and 72 parts of 80 mesh iron powder, and the resulting mixture was heated to 95° C. and kept at this temperature for 0.5 hour. Subsequently, (III-2) was added at that temperature over a period of 1 hour, and the resulting mixture was kept at that temperature for an additional 1 hour. The mixture was cooled to 70° C., neutralized with sodium hydrogen carbonate, and filtered to remove the iron slurry. Since the filtrate thus obtained separated into two layers, the oily layer was withdrawn.

Thus, 88 parts of 2-aminophenyl-β-hydroxyethylsulfone was obtained.

Its yield was 87% based on o-nitrochlorobenzene.

EXAMPLE 4

To 160 parts of dimethylformamide having a water content of 3%, 158 parts of p-nitrochlorobenzene was added and then 94 parts of mercaptoethanol was added. Temperature of the mixture was elevated to 45° C. Then, 41 parts of powdery sodium hydroxide was added over a period of 4 hours. After adding it, the mixture was kept at that temperature for an additional 1 hour. After completion of the reaction, the reaction mixture was neutralized, the deposited sodium chloride was filtered off, and the filtrate was subjected to flash-distillation to remove dimethylformamide.

Thus, 193 parts of 4-nitrophenyl-β-hydroxyethylsulfide (IV-1) was obtained. Its yield was 97%. After adding (IV-1) to 390 parts of acetonitrile, 275 parts of 30% hydrogen peroxide solution was added thereto over a period of 1 hour, while keeping the system at 40° C. During this period, 10% aqueous solution of sodium carbonate was added in order to keep the pH of system at 9.0. After adding the hydrogen peroxide solution, the resulting mixture was kept at that temperature for an additional 3 hours. After completion of the reaction, acetonitrile was distilled off, and the resulting 4-nitrophenyl-β-hydroxyethylsulfone (IV-2) was taken out from the system by filtration. Then, it was placed in a stainless autoclave together with 1,000 parts by volume of methanol and 2.5 parts of Raney's nickel catalyst, and subjected to reductive hydrogenation reaction at 80° C. under a pressure of 30 kg/cm². The reduction reaction took 8 hours. After removing solid matters such as catalyst from the reaction mixture by filtration at high temperature and then distilling off the methanol, the mixture was cooled. Thus, 185 parts of 4-aminophenyl-β-hydroxyethylsulfone was obtained.

Its over-all yield from p-nitrochlorobenzene was 91%.

EXAMPLE 5

To 160 parts of dimethyl sulfoxide having a water content of 5%, 158 parts of p-nitrochlorobenzene was added and then 115 parts of mercaptoethanol was added. Temperature of the mixture was elevated to 50° C. Then, 41 parts of powdery sodium hydroxide was added over a period of 5 hours. After adding it, the mixture was kept at that temperature for an additional 1 hour. After completion of the reaction, the reaction mixture was neutralized, the deposited sodium chloride was filtered off, and then the filtrate was subjected to flash distillation to remove dimethyl sulfoxide.

Thus, 191 parts of 4-nitrophenyl-β-hydroxyethylsulfide (V-1) was obtained. Its yield was 96%.

Then, (V-1) was added to a solution previously prepared by mixing a solution of 2 parts of sodium tungstate in 380 parts of water with 570 parts of acetonitrile. Subsequently, 272 parts of 30% hydrogen peroxide solution was added dropwise thereinto over a period of 2 hours, while keeping the system at 45° C. Thereafter, the mixture was kept at that temperature for an additional 3 hours. After completion of the reaction, the acetonitrile was distilled off, and the resulting 4-nitrophenyl-β-hydroxyethylsulfone (V-2) was taken out from the system by filtration. Its yield was 206 parts.

Then, (V-2) was mixed with 1030 parts of methanol and 2 parts of Raney's nickel catalyst, and subjected to reductive hydrogenation reaction at 80° C. under a pressure of 30 kg/cm². The reaction took 8 hours. After filtering off solid matters such as catalyst from the reaction mixture, the solvent was distilled off.

Thus, 178 parts of 4-aminophenyl-β-hydroxyethylsulfone was obtained.

Its yield was 88% based on p-nitrochlorobenzene.

EXAMPLE 6

To a mixture consisting of 160 parts of dimethylformamide and 8 parts of water, 158 parts of p-nitrochlorobenzene was added and then 94 parts (1.2 times by mole) of mercaptoethanol was added. Temperature of the resulting mixture was elevated to 50° C. Subsequently, 41 parts (1.01 times by mole) of powdery sodium hydroxide was added over a period of 4 hours. After adding it, the resulting mixture was kept at that temperature for an additional 1 hour. After completion of the reaction, the reaction mixture was neutralized, the deposited sodium chloride was filtered off, and the filtrate was subjected to flash distillation to remove dimethylformamide.

Thus, 193 parts of 4-nitrophenyl-β-hydroxyethylsulfide was obtained. Its yield was 96%.

Then, it was oxidized and reduced in the same way as in Example 1 to obtain 180 parts of 4-aminophenyl-β-hydroxyethylsulfone.

Its yield was 89% based on p-nitrochlorobenzene.

EXAMPLE 7

To 80 parts of dimethylformamide, 79 parts of o-nitrochlorobenzene was added and then 47 parts (1.2 times by mole) of mercaptoethanol was added. Temperature of the mixture was elevated to 40° C. Then, 44 parts of 48% aqueous solution of sodium hydroxide (1.05 times by mole) was added over a period of 5 hours. Thereafter, the mixture was kept at that temperature for an additional 1 hour. After completion of the reaction, the reaction mixture was neutralized, water was distilled off, the deposited sodium chloride was filtered off, and dimethylformamide was distilled off from the filtrate. Thus, 96 parts of 2-nitrophenyl-$\beta$-hydroxyethylsulfide was obtained. Its yield was 96%.

Then, it was oxidized and reduced in the same way as in Example 1 to obtain 94 parts of 2-aminophenyl-$\beta$-hydroxyethylsulfone.

Its yield was 93% based on o-nitrochlorobenzene.

EXAMPLE 8

To 160 parts of dimethylformamide, 158 parts of p-nitrochlorobenzene was added and then 94 parts (1.2 times by mole) of mercaptoethanol was added. Temperature of the mixture was elevated to 40° C.

Subsequently, 83 parts (1.02 times by mole) of 49% aqueous solution of sodium hydroxide was added over a period of 5 hours. Thereafter, the reaction mixture was neutralized, water was distilled off, the deposited sodium chloride was filtered off, and the filtrate was subjected to flash distillation to remove dimethylformamide. Thus, 190 parts of 4-nitrophenyl-$\beta$-hydroxyethylsulfide was obtained. Its yield was 95%.

Then, it was oxidized and reduced in the same way as in Example 4 to obtain 180 parts of 4-aminophenyl-$\beta$-hydroxyethylsulfone.

Its yield was 89% based on p-nitrochlorobenzene.

EXAMPLE 9

To 80 parts of dimethylacetamide having a water content of 3%, 79 parts of p-nitrochlorobenzene was added and then 47 parts (1.2 times by mole) of mercaptoethanol was added. Temperature of the mixture was elevated to 50° C. Then, 29 parts (1.03 times by mole) of powdery potassium hydroxide was added over a period of 4 hours. Thereafter, the resulting mixture was kept at that temperature for an additional 1 hour. After completion of the reaction, the reaction mixture was neutralized, the deposited inorganic salt was filtered off, and then dimethylacetamide was distilled off. Thus, 95 parts of 4-nitrophenyl-$\beta$-hydroxyethylsulfide was obtained.

Then, it was oxidized and reduced in the same way as in Example 1 to obtain 91 parts of 4-aminophenyl-$\beta$-hydroxyethylsulfone.

Its yield was 90% based on p-nitrochlorobenzene.

EXAMPLE 10

To a mixture consisting of 160 parts of N-methyl-2-pyrrolidone and 8 parts of water, 158 parts of o-nitrochlorobenzene was added and then 94 parts (1.2 times by mole) of mercaptoethanol was added. Temperature of the resulting mixture was elevated to 45° C.

Subsequently, 41 parts (1.01 times by mole) of powdery sodium hydroxide was added over a period of 5 hours. Thereafter, the mixture was kept at that temperature for an additional 1 hour. After completion of the reaction, the reaction mixture was neutralized, the deposited sodium chloride was filtered off, and then the filtrate was subjected to flash distillation to remove the N-methyl-2-pyrrolidone.

Thus, 192 parts of 2-nitrophenyl-$\beta$-hydroxyethylsulfide was obtained. Its yield was 96%.

Then, it was oxidized and reduced in the same way as in Example 1 to obtain 183 parts of 2-aminophenyl-$\beta$-hydroxyethylsulfone.

Its yield was 90% based on o-nitrochlorobenzene.

EXAMPLE 11

Ninety parts of 4-nitrophenyl-$\beta$-hydroxyethylsulfide (purity 89%) produced by the procedure of Example 1 was added to a mixture consisting of 240 parts of acetonitrile and 80 parts of water.

At 40° C., 114 parts (2.5 times by mole) of 30% hydrogen peroxide solution was added dropwise thereinto over a period of 1 hour. During this period, 10% aqueous solution of sodium carbonate was added to maintain pH of the system at 9.0. Thereafter, the resulting mixture was kept at that temperature for an additional 3 hours, while maintaining pH of the system at 9.0. The amount of 10% aqueous solution of sodium carbonate necessary for maintaining said pH value during this period was 150 parts.

Thus, the intended sulfone was formed in a yield of 100%, and there remained no starting sulfide nor intermediate sulfoxide.

After distilling off the acetonitrile from the reaction mixture under a reduced pressure, the residue was concentrated, cooled, filtered and dried.

Thus, 88 parts of 4-nitrophenyl-$\beta$-hydroxyethylsulfone was obtained as a white crystalline product.

Its yield was 94%.

Then, it was reduced in the same way as in Example 1 to obtain 76 parts of 4-aminophenyl-$\beta$-hydroxyethylsulfone, Its yield was 93% based on 4-nitrophenyl-$\beta$-hydroxyethylsulfide.

EXAMPLE 12

Forty parts of the 2-nitrophenyl-$\beta$-hydroxyethylsulfide obtained by the procedure of Example 3 was added to a mixture prepared by adding 120 parts of acetonitrile to a uniform solution of 0.2 part of tungstic acid in 120 parts of water.

At 50° C., 57 parts (2.5 times by mole) of 30% hydrogen peroxide solution was added thereto over a period of 1 hour. Thereafter, the resulting mixture was kept at that temperature for an additional 3 hours.

Thus, the intended sulfone was formed in a yield of 100%, and there remained no starting sulfide nor intermediate sulfoxide.

After distilling off the acetonitrile from the reaction mixture under a reduced pressure, the residue was concentrated, cooled, filtered and dried.

Thus, 44 parts of 2-nitrophenyl-$\beta$-hydroxyethylsulfone was obtained as a white crystalline product.

Its yield was 94%.

Then, it was reduced in the same way as in Example 1 to obtain 37 parts of 2-aminophenyl-$\beta$-hydroxyethylsulfone.

Its yield was 92% based on 2-nitrophenyl-$\beta$-hydroxyethylsulfide.

What is claimed is:

1. A process for producing aminophenyl-$\beta$-hydroxyethylsulfone of the formula (I),

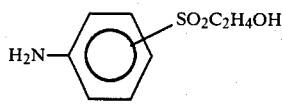

which comprises:

(1) condensing a nitrohalobenzene with mercaptoethanol in the presence of an alkali hydroxide and at least one reaction medium selected from N-alkyl-substituted amides and sulfoxides to produce mononitrophenyl-β-hydroxyethylsulfide of the formula (II),

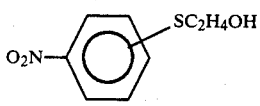

(2) oxidizing the mononitrophenyl-β-hydroxyethylsulfide (II) to produce mononitrophenyl-β-hydroxyethylsulfone of the formula (III),

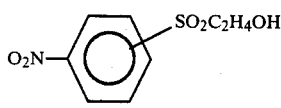

and (3) reducing the mononitrophenyl-β-hydroxyethylsulfone to produce the aminophenyl-β-hydroxyethylsulfone of the formula (I).

2. The process according to claim 1, wherein mercaptoethanol is used in an amount of ranging from 1 through 3 moles per mole of the nitrohalobenzene.

3. The process according to claim 1, wherein the alkali hydroxide is sodium hydroxide or potassium hydroxide.

4. The process according to claim 1, wherein the alkali hydroxide is used in an amount of ranging from 1 through 1.2 mole per mole of the nitrohalobenzene.

5. The process according to claim 1, wherein the reaction medium has a water content of 2 to 30% by weight.

6. The process according to claim 1, wherein the condensing is carried out at a temperature of 30° to 55° C.

7. The process according to claim 1, wherein the oxidizing is carried out using hydrogen peroxide in a reaction medium of water or an aqueous reaction medium comprising at least one nitrile in the presence of a basic compound or a metal catalyst.

8. The process according to claim 7, wherein the oxidizing is carried out in a reaction medium of water at a temperature of 30° to 100° C. at an initial pH of 3 to 8.

9. The process according to claim 7, wherein the oxidizing is carried out in a nitrile-containing aqueous reaction medium at a temperature of 30° to 65° C., while controlling the pH of the reaction system to 7.5 to 10.5.

10. The process according to claim 7, wherein the oxidizing is carried out in the nitrile-containing aqueous reaction medium in the presence of a metal catalyst.

11. The process according to claim 1, wherein the reducing is carried out by a catalytic reduction method.

* * * * *